(12) United States Patent
Doty et al.

(10) Patent No.: US 8,469,293 B2
(45) Date of Patent: Jun. 25, 2013

(54) DIGITAL ODOR GENERATOR

(76) Inventors: Richard L. Doty, Philadelphia, PA (US); Aaron Scott, Columbia, MO (US); Ling Zhou, Bronx, NY (US)

(*) Notice: Subject to any disclaimer, the term of this patent is extended or adjusted under 35 U.S.C. 154(b) by 475 days.

(21) Appl. No.: 12/799,034

(22) Filed: Apr. 16, 2010

(65) Prior Publication Data

US 2011/0253800 A1 Oct. 20, 2011

(51) Int. Cl.
*A62C 31/00* (2006.01)
*A24F 25/00* (2006.01)
*A61L 9/04* (2006.01)

(52) U.S. Cl.
USPC ............ 239/448; 239/44; 239/51.5; 239/441; 422/124

(58) Field of Classification Search
USPC ................. 239/44–45, 48, 51.5, 52, 418, 436, 239/441, 448–449; 261/30, DIG. 65; 422/124
See application file for complete search history.

(56) References Cited

U.S. PATENT DOCUMENTS

| | | | | |
|---|---|---|---|---|
| 2,552,887 | A * | 5/1951 | Demonet et al. | 261/99 |
| 4,265,248 | A | 5/1981 | Chuiton et al. | |
| 4,934,386 | A | 6/1990 | Walker et al. | |
| 5,023,020 | A * | 6/1991 | Machida et al. | 261/18.1 |
| 5,457,983 | A | 10/1995 | Sauvageau et al. | |
| 5,565,148 | A * | 10/1996 | Pendergrass, Jr. | 261/30 |
| 5,591,409 | A | 1/1997 | Watkins | |
| 5,805,768 | A * | 9/1998 | Schwartz et al. | 392/390 |
| 6,325,475 | B1 | 12/2001 | Hayes et al. | |
| 6,338,715 | B1 | 1/2002 | Hayes et al. | |
| 6,390,453 | B1 | 5/2002 | Frederickson et al. | |
| 6,568,659 | B2 * | 5/2003 | Hugon | 261/30 |
| 6,672,129 | B1 | 1/2004 | Frederickson et al. | |
| 6,979,298 | B2 | 12/2005 | Vodyanoy et al. | |
| 7,152,758 | B2 | 12/2006 | Fazzio et al. | |

OTHER PUBLICATIONS

Osmic Enterprises, Inc., "OLFACT-ID/D" 2008.
Osmic Enterprises, Inc., "OLFACT—Combo" 2008.

* cited by examiner

*Primary Examiner* — Len Tran
*Assistant Examiner* — Justin Jonaitis
(74) *Attorney, Agent, or Firm* — Norman E. Lehrer

(57) ABSTRACT

A digital odor generator includes a housing and a cylindrically shaped odor chamber carried by the housing and including a plurality of separate odor compartments isolated from each other. A porous hollow cylinder, made of plastic or some other porous material, with an odorant therein is located in each of the odor compartments. A nozzle in the form of a truncated cone is operatively connected to the odor chamber. The nozzle includes an outer face having an enlarged central opening and a plurality of smaller openings surrounding the central opening; the number of smaller openings being equal to the number of odor compartments. The outer face of the nozzle is arranged so that a person can position his or her nose near the openings. Each of the smaller openings is associated with a different one of the odor compartments and is isolated from the others and from the central opening so that the odor from only one odor compartment can be emitted through only one of the smaller openings. A fan within the housing is adapted to pass fresh air through the central opening. And an air pressure source selectively forces one or more of the odorants through their respective odor compartments and out of the nozzle.

16 Claims, 6 Drawing Sheets

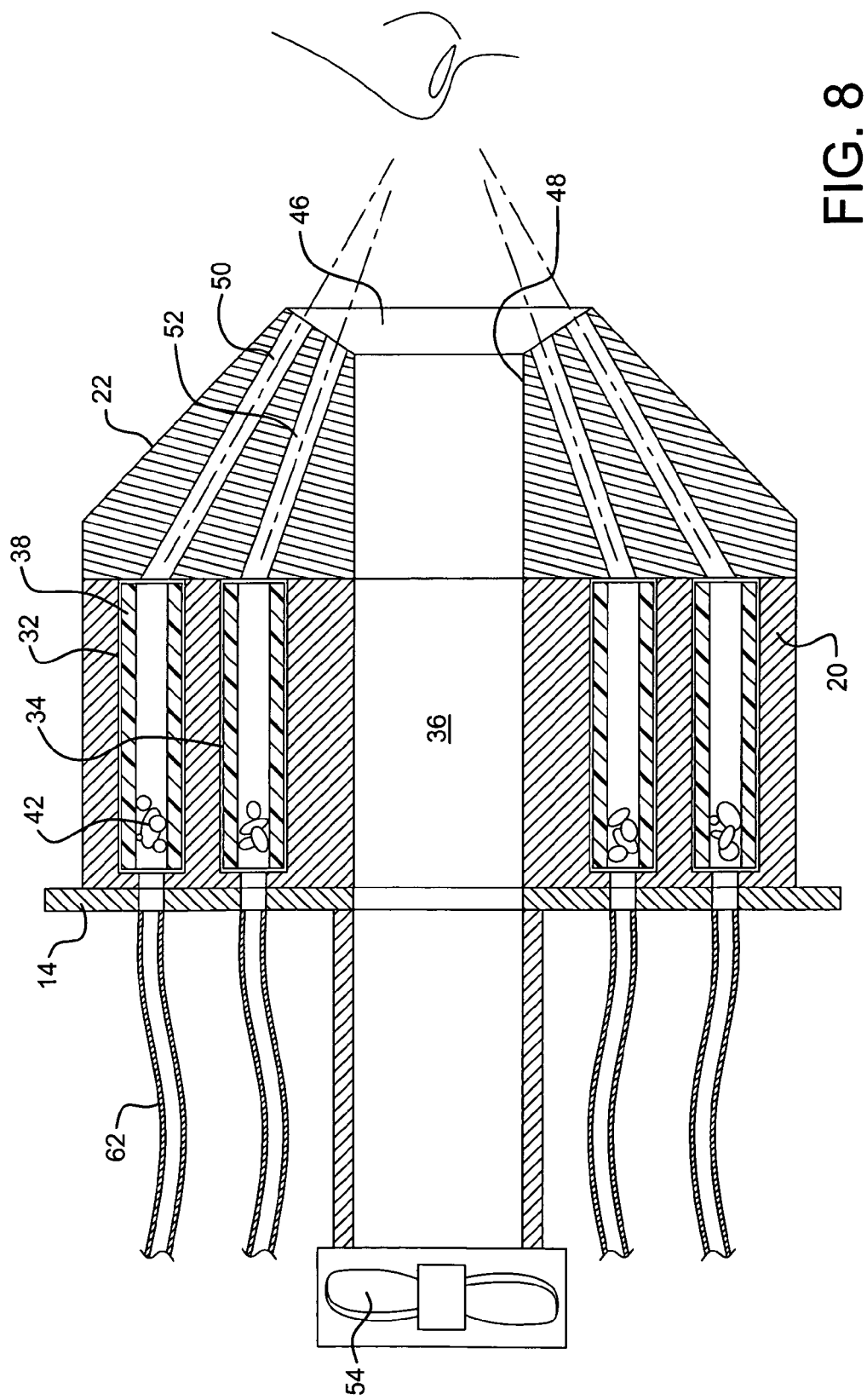

DIGITAL ODOR GENERATOR

BACKGROUND OF THE INVENTION

The present invention is directed toward a digital odor generator or olfactometer and, more particularly, toward a digital odor generator that can be used to administer various odors alone or in various combinations to a patient or subject. The digital odor generator of the invention can also be used to administer olfactory tests remotely over the Internet or other network and to collect the results and tabulate data over such networks.

The ability to smell various odors and to distinguish odors from each other is obviously important in our every day lives. The sense of smell, which largely influences the flavor of foods, is associated with emotion, with nutrition, with quality of life, and with safety from spoiled foods, leaking natural gas, fire, and other hazardous situations. Loss of smell or the reduced ability to smell, therefore, can significantly impact everyday life. People who lose the sense of smell have major elements of their lives compromised and often become psychologically depressed.

Quantitative tests of the sense of smell can be useful as diagnostic tools. The measurement of olfactory thresholds, for example, is beneficial in the early detection and management of a number of diseases and disorders. Among these are damage to the olfactory system, such as the olfactory nerves or olfactory bulb, by head trauma, neurodegenerative diseases such as Alzheimer's disease and Parkinson's disease, acute viral and/or bacterial infections, exposure to toxic fumes and chemicals, side-effects from radiation therapy to the head, and others. A medical diagnostic instrument that can measure olfactory thresholds and other indices of olfactory function in an accurate manner, quickly and at a relatively low cost, would therefore be beneficial. Such an instrument could be used not only as a one time evaluation of a patient, but it could be used to trace a patient's progress over time to monitor for onset of a particular occurrence.

The measurement of olfactory function has been accomplished by various means. One method is by using scratch-and-sniff pads where the test operator scratches the surface to expose the odor, puts it up to the patient's nose, and asks for a response. Another test method is using squeeze-bottle or sniff bottle smell test kits. In the case of threshold testing, a series of bottles with increasing concentration of vapors is used. In most such methods the manner of stimulus presentation, which can be influenced by the test administrator, as well as the freshness of the samples, are critical factors in the test results. Obtaining good quantitative test results is frequently difficult with these methods. Another method is the use of a large research-type olfactometer. The disadvantage to this method is that the test is slow and the cost of the instrument is very high. Furthermore, the test must be administered by a trained professional.

Smaller olfactometers have been proposed and are described in various patent documents. For example, the following U.S. Patents have issued for alleged improvements to olfactometers: U.S. Pat. No. 4,265,248 to Chuiton et al.; U.S. Pat. No. 5,565,148 to Pento Fadergrass, Jr.; U.S. Pat. Nos. 6,390,453 and 6,672,129 to Frederickson et al. and U.S. Pat. No. 7,152,758 to Fazzio et al. To applicant's knowledge, none of these devices have ever been commercialized. They would appear to be either too complicated, ineffective or too expensive to produce.

Applicant is aware of an olfactometer that has become commercially available from Osmic Enterprises, Inc. of Cincinnati, Ohio, and that is alleged to be useful for assessing odor threshold, identification, discrimination, and memory. The number of odors available is limited and its design makes it difficult to change or add odors, thereby requiring that the entire machine be returned to the manufacturer if such changes need to be made. The unit also has to be returned to the manufacturer every six months for recharging. Even further, the unit utilizes a single dispensing nozzle which could cause cross contamination and thereby decrease the accuracy of the tests. This device is unable to present combinations of odors to the subject to determine how mixtures influence the overall smell sensation.

Therefore, a need exists for an olfactometer that is easy and convenient to use and maintain, which can present more than one odorant stimulus in a mixture at a time, which can allow for rapid changing of sets of odorants between subjects or patients, which can accurately present smell stimuli to subjects, and which can be used to administer smell tests remotely over the Internet or other network and subsequently collect the results and tabulate data over the Internet.

SUMMARY OF THE INVENTION

The present invention is designed to overcome the deficiencies of the prior art discussed above. Accordingly, it is an object of the invention to provide an accurate digital odor generator that can be use to easily administer various odor or smell tests to a subject.

It is a further object of the present invention to provide a digital odor generator that can also be used to administer tests remotely over the Internet or other network and which can be used to collect the results of the tests and tabulate data over the Internet.

It is a still further object of the invention to provide a digital odor generator that can be use to easily administer various odor or smell tests to a subject and which can be easily and quickly replenished when necessary.

It is a still further object of the invention to provide a device so that different sets of odorants or odorant concentrations can be quickly changed between test subjects or administrations to allow for practicality and flexibility in the stimuli to be presented and the tests to be administered.

In accordance with the illustrative embodiments demonstrating features and advantages of the present invention, there is provided a digital odor generator which includes a housing and a cylindrically shaped odor chamber carried by the housing. The chamber also includes a plurality of separate odor compartments isolated from each other. A porous hollow cylinder, made of plastic or other material in its preferred embodiment, with an odorant contained therein is located in each of the odor compartments. A nozzle in the form of a truncated cone is operatively connected to the odor chamber. The nozzle includes an outer face having an enlarged central opening and a plurality of smaller openings surrounding the central opening; the number of smaller openings being equal to the number of odor compartments. The outer face of the nozzle is arranged so that a person can position his or her nose near the openings. Each of the smaller openings is associated with a different one of the odor compartments and is isolated from the others and from the central opening so that the odor from only one odor compartment can be emitted through only one of the smaller openings. A fan within the housing is adapted to pass fresh air through the central opening. And an air pressure source selectively forces an odor from one of the odorants through its respective odor compartment and out of the nozzle.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawing one form which is presently preferred; it being understood that the invention is not intended to be limited to the precise arrangements and instrumentalities shown.

FIG. 8 is a partial cross-sectional view taken through the lines 8-8 of FIG. 2.

DETAILED DESCRIPTION OF THE PREFERRED EMBODIMENT

Figure 1:
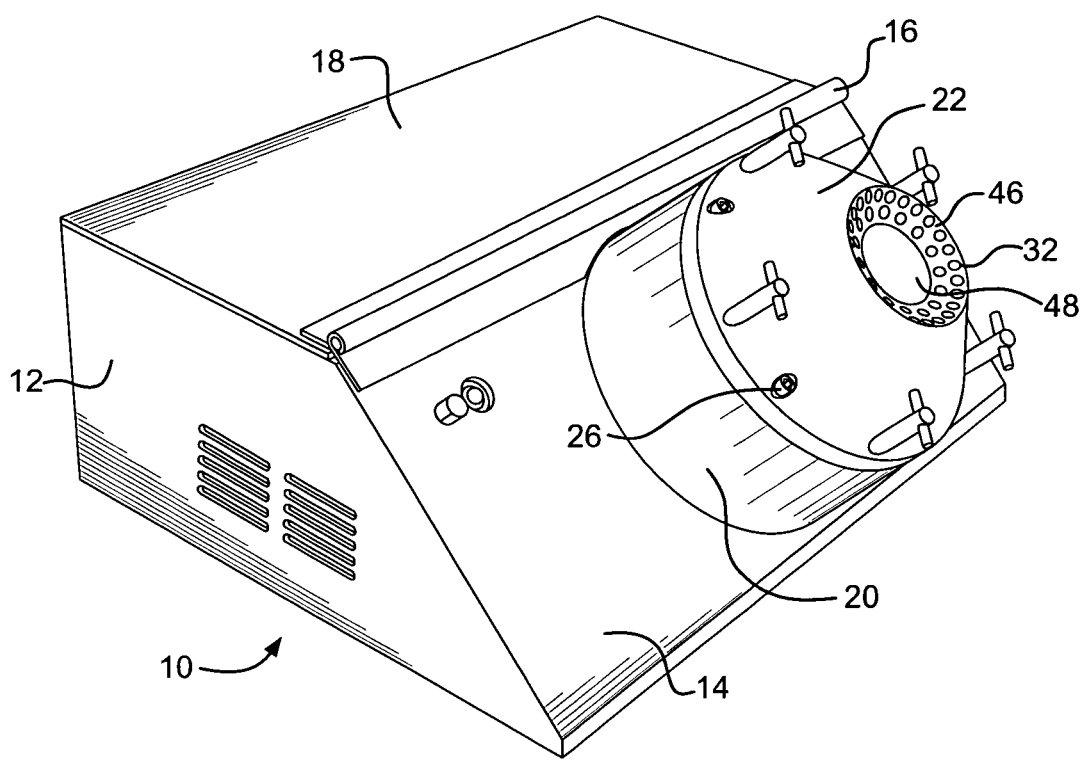
FIG. 1 is a front perspective view of the digital odor generator or olfactometer or the present invention.
Figure 2:
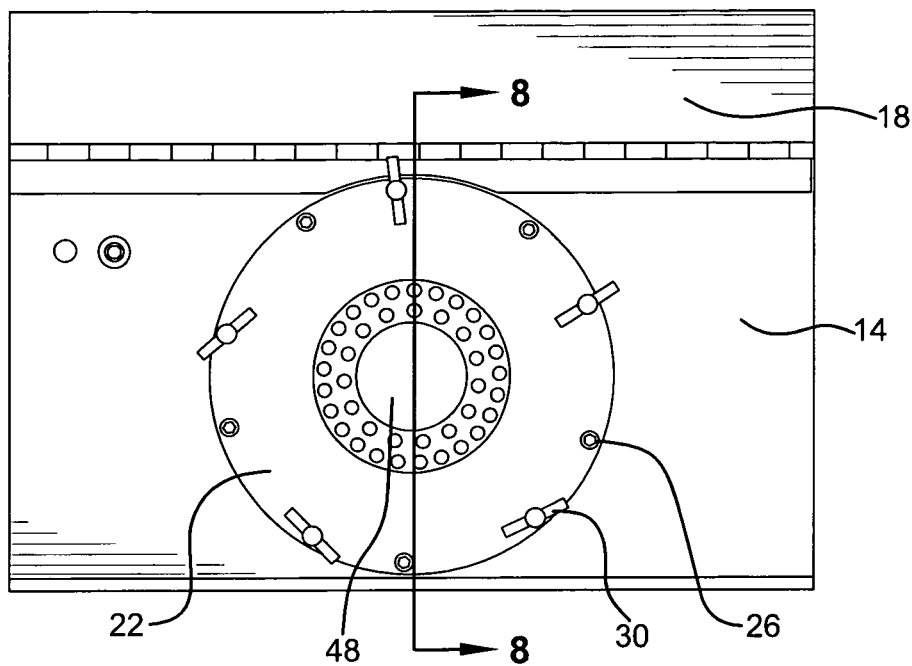
FIG. 2 is front view of the face of the digital odor generator or olfactometer showing the nozzle portion of the same.
Figure 7:
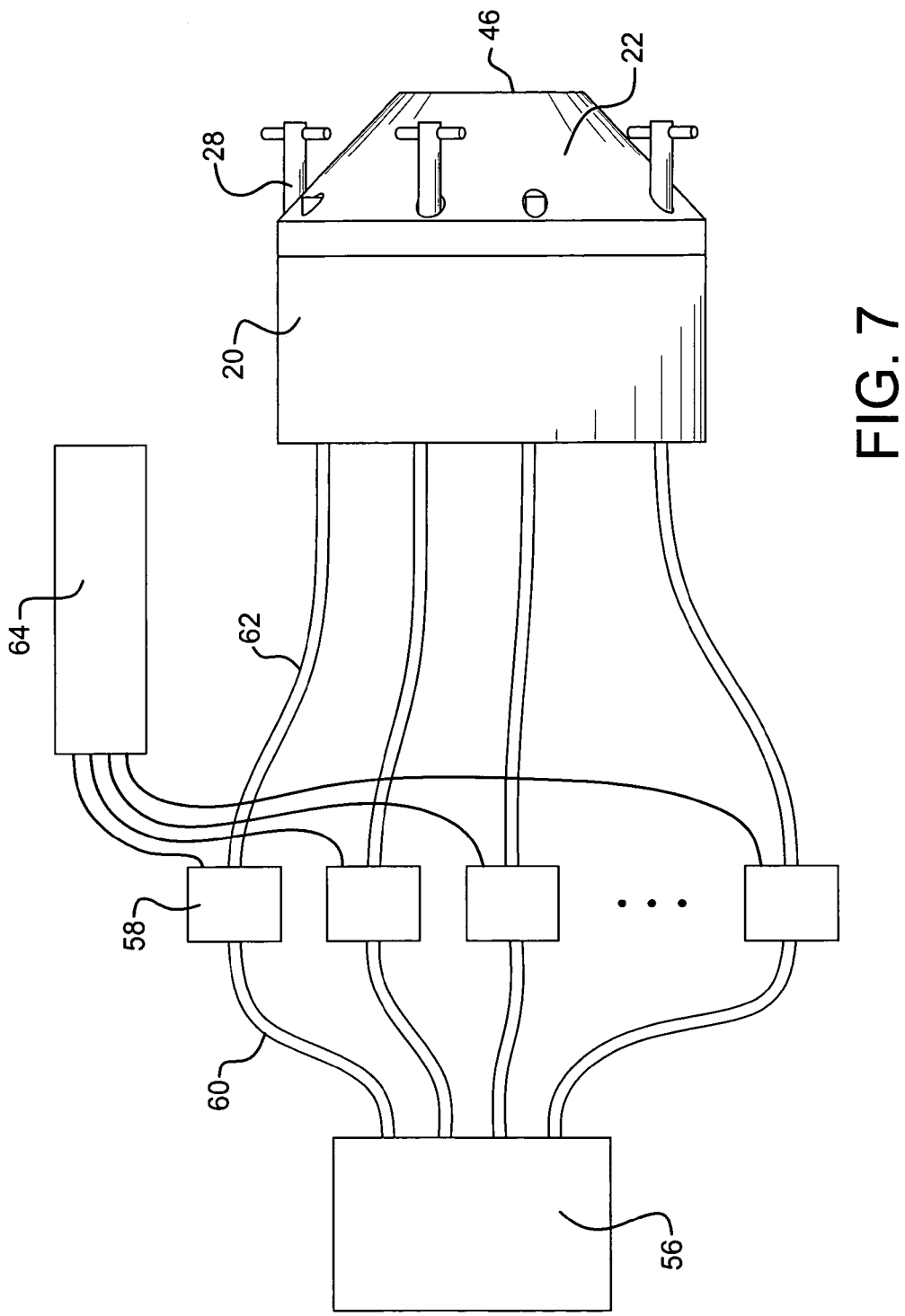
FIG. 7 is a schematic representation illustrating the overall operation of the digital odor generator of the invention.

Referring now to the drawings in detail wherein like reference numerals have been used throughout the various figures to designate like elements, there is shown in FIGS. 1 and 7 a digital odor generator or olfactometer constructed in accordance with the principles of the present invention and designated generally as 10. The digital odor generator 10 is comprised essentially of a housing 12 which, in the preferred embodiment, is comprised of a substantially rectangularly shaped box having a slanted front wall 14 hinged at 16 to the top 18. Secured to the slanted front wall 14 is a substantially cylindrically shaped odor chamber 20. A nozzle 22, which is essentially in the shape of a truncated cone is secured to the flat circular outer surface 24 (see FIG. 4) of the odor chamber 20.

Figure 4:
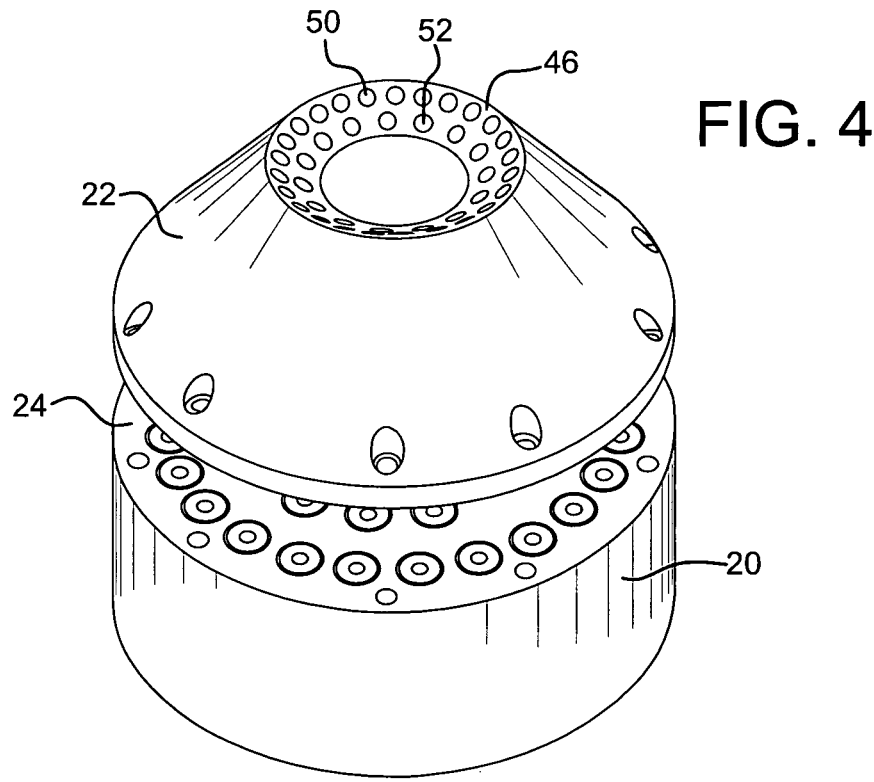
FIG. 4 is an exploded view showing the nozzle separated from the odor chamber.
Figure 5:
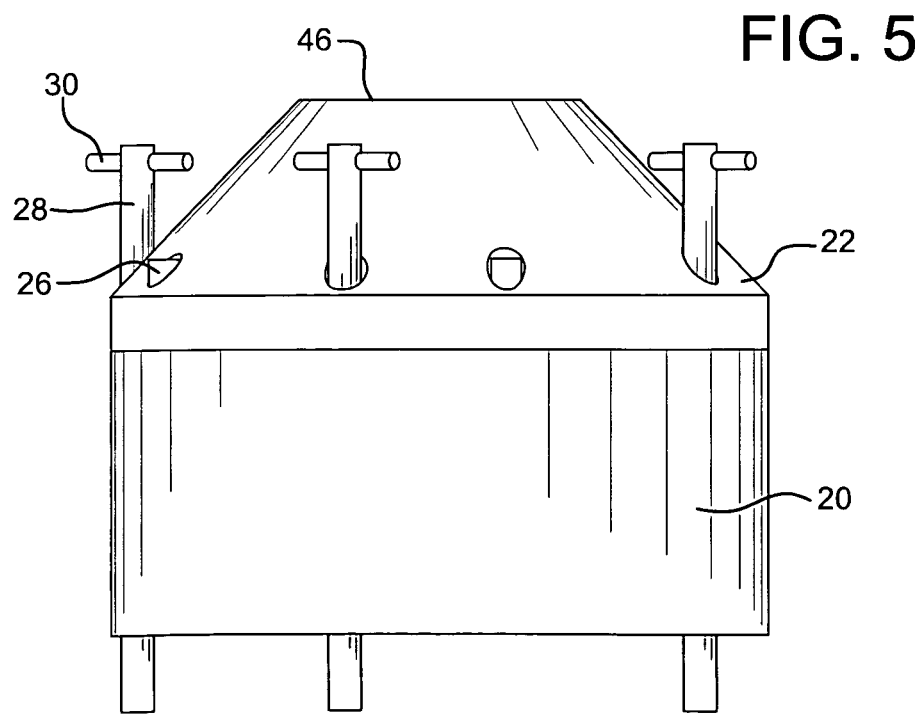
FIG. 5 is an elevational view of the combined nozzle and odor chamber.

As shown most clearly in FIGS. 1, 4 and 5, the nozzle 22 is preferably secured to the odor chamber 20 through the use of a plurality of short bolts 26. The assembly of the odor chamber 20 and the nozzle 22 is then secured to the front face 14 of the housing 12 through the use of elongated bolts 28. The bolts 28 preferably have a handle 30 formed at the top thereof so that the assembly can be attached to or removed from the housing 12 whenever desired without the use of tools. While a specific number of bolts 26 and 30 are illustrated in the drawings, it should be readily apparent that any number could be used that will securely attach the parts together. Furthermore, means other than bolts could be utilized and some elements of the configuration could be combined into single entities; for example, the nozzle and the odor chamber could be manufactured as one element.

Figure 3:
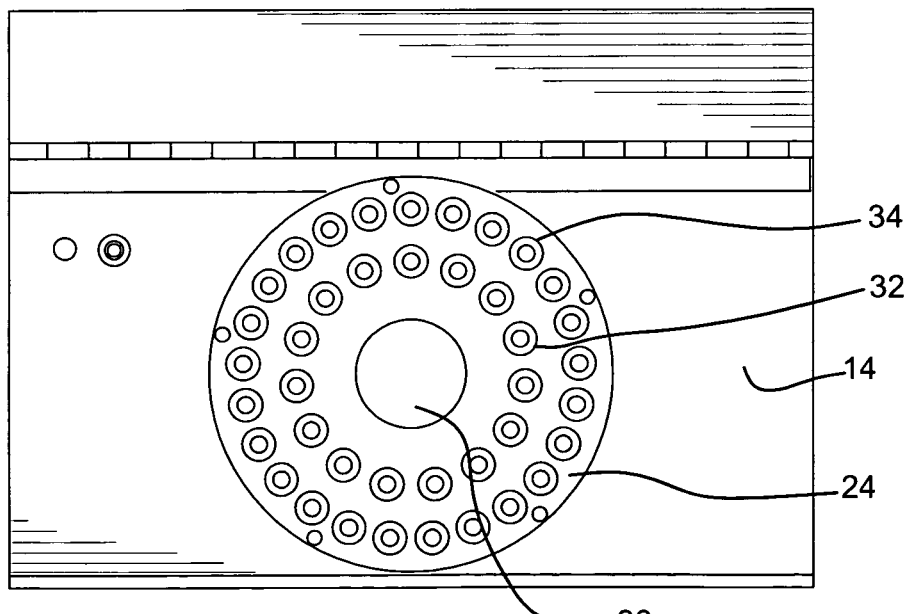
FIG. 3 is view similar to FIG. 2 but with the nozzle removed to expose the odor chamber.
Figure 6:
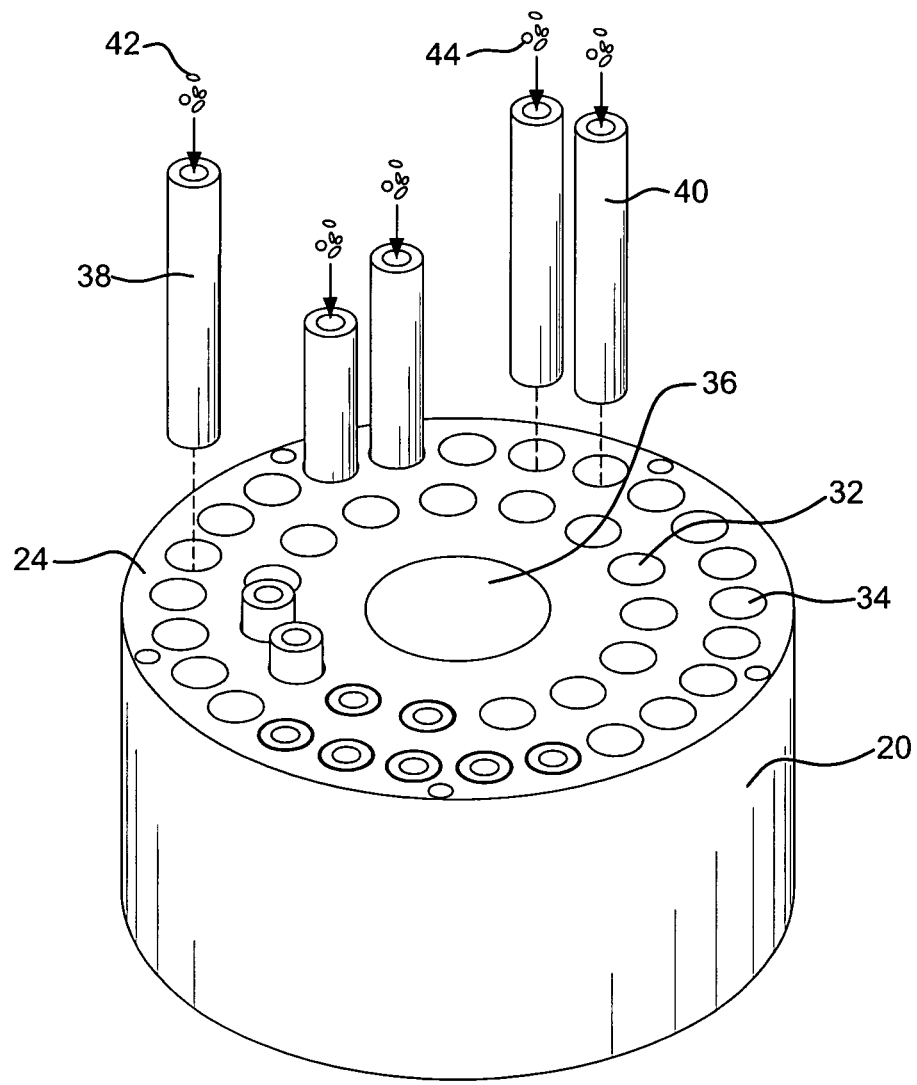
FIG. 6 is an exploded view of the odor chamber illustrating how the various odor cartridges are inserted therein.

The odor chamber 20 includes a plurality of separate odor compartments such as shown at 32 and 34. As shown in FIGS. 3 and 6, in the preferred embodiment of the invention, there are forty odor chambers that are formed in two circular rings that surround a central opening 36 in the odor chamber 20. This arrangement is, of course, by way of example only. Fewer than forty or more than forty odor compartments could be included.

Each of the odor compartments is in the form of an elongated cylindrical cavity which is open at the top surface 24 of the odor chamber 20. The axis of each of the elongated cylindrical cavities are parallel to the axis of the central opening 36 and are also parallel to the central axis of the odor chamber 20.

Each of the odor compartments 32 and 34 includes an odorant therein. In the preferred embodiment of the invention, this is accomplished utilizing a plurality of porous polyethylene hollow cylinders such as shown at 38 and 40. A different cylinder 38 or 40 is, of course, inserted into a different one of the odor compartments 32 or 34 and each plastic cylinder includes an odorant, schematically shown at 42 and 44, in the hollow center thereof.

A different odorant 42 or 44 is, of course, utilized in each of the porous cylinders 38 and 40. Furthermore, because of the arrangement and separation of the odor compartments 32 and 34 in combination with the nozzle as will be explained in more detail below, each of the odorants is separated from each of the other odorants. Thus, there can be no cross contamination of odors.

The details of the nozzle 22 will be understood most clearly from FIGS. 4 and 8. The nozzle 22 includes an outer face 46 that includes an enlarged central opening 48 passing therethrough and a plurality of smaller cylindrical openings 50 and 52. The central opening 48 is in alignment with the central opening 36 in the odor chamber 20 and each of the openings 50 and 52, which are in the form of elongated cylindrical passages, are in communication with a different one of the odor compartments 32 and 34 in the odor chamber 20.

Contained within the housing 12 is a fan 54 which is adapted to force fresh air through the central openings 36 and 48 of the odor chamber 20 and nozzle 22. Also contained within the housing, as is schematically represented in FIG. 7, are a source of air pressure 56 and a plurality of valves 58. The number of valves 58 is equal to the number of odor compartments 32 or 34. Appropriate tubing such as shown, for example, at 60 and 62 connects the air pressure source 56 to the individual odor compartments when its respective valve 58 is operated. An electronic controller 64 controls which valve 58 will be open. The controller 64 also operates the fan 54 and can be controlled remotely over the Internet or some other communications system.

When one of the valves 58 is activated, air pressure passes through the tubing 60 and 62 and forces odor from the odorant contained within the respective odor compartment to pass through the associated passageway such as passageway 50 or 52 as shown in FIG. 4 and out of the associated nozzle opening. As most clearly shown in FIG. 8, the passageways or nozzle openings 50 and 52 are substantially parallel to the outer conical shape of the nozzle 22. As a result, air, along with its respective odorant, is directed toward a focal point which is located just outside of the nozzle where a patient will position his or her nose.

By controlling the valves 58, which can be done remotely, the amount or intensity of the odorant emitted from a nozzle opening 50 or 52 can be controlled as can the duration that the particular odorant is emitted. Similarly, the valves 58 allow any one or any desired combination of odorants to be emitted, singularly, in combination or in a desired sequence.

The present invention may be embodied in other specific forms without departing from the spirit or essential attributes thereof and accordingly, reference should be made to the appended claims rather than to the foregoing specification as indicating the scope of the invention.

We claim:

1. A digital odor generator comprising:
a housing;
an odor chamber carried by said housing, said odor chamber including a plurality of separate odor compartments isolated from each other;
a nozzle means in the form of a truncated cone including a circular base operatively associated with said odor chamber, said nozzle means having an outer face including an enlarged central opening and a plurality of smaller openings surrounding said central opening, the number of said smaller openings being equal to the number of said odor compartments, the outer face of said nozzle means being arranged so that a person can position his or her nose near said openings;
each of said smaller openings being associated with a different one of said odor compartments and being isolated from the others of said other odor compartments and from said central opening whereby the odor from only one odor compartment can be emitted through only one of said smaller openings;
said nozzle means including a plurality of passageways therein, each of said passageways being associated with a different one of said smaller openings and connecting said openings to said odor compartments, each of said passageways being parallel to the outer surface of said cone and being arranged in a circular pattern, each of said passageways including a central axis wherein the central axes of all of said passageways converge at a point outwardly of said outer face of said nozzle and in line with said enlarged central opening, and
means within said housing for passing fresh air through said central opening.

2. The digital odor generator as claimed in claim 1 wherein said odor chamber is in the form of a cylinder including a flat circular outer surface.

3. The digital odor generator as claimed in claim 2 wherein said circular base is the same size as said circular surface.

4. The digital odor generator as claimed in claim 3 further including means for securing said nozzle to said odor chamber.

5. The digital odor generator as claimed in claim 4 wherein each of said odor compartments is in the form of an elongated cylindrical cavity open at said surface.

6. The digital odor generator as claimed in claim 5 wherein said odor chamber includes a central opening that aligns with the central opening in said nozzle means.

7. The digital odor generator as claimed in claim 6 wherein each of said odor compartments includes an odorant therein.

8. The digital odor generator as claimed in claim 7 further including a plurality of porous hollow cylinders adapted to fit within said odor compartments and wherein said odorants are located within each of said hollow cylinders.

9. The digital odor generator as claimed in claim 8 wherein said hollow cylinders are comprised of a porous plastic.

10. The digital odor generator as claimed in claim 7 including means for selectively forcing one or more odors through their respective odor compartments and out of said nozzle.

11. A digital odor generator comprising:
a housing;
an odor chamber carried by said housing, said odor chamber including a plurality of separate odor compartments isolated from each other;
a nozzle means operatively associated with said odor chamber, said nozzle means having an outer face including an enlarged central opening and a plurality of smaller openings surrounding said central opening, the number of said smaller openings being equal to the number of said odor compartments, the outer face of said nozzle means being arranged so that a person can position his or her nose near said openings;
each of said smaller openings being associated with a different one of said odor compartments and being isolated from the others of said other odor compartments and from said central opening whereby the odor from only one odor compartment can be emitted through only one of said smaller openings;
said nozzle means including a plurality of passageways therein, each of said passageways being associated with a different one of said smaller openings and connecting said smaller openings to said odor compartments, each of said passageways including a central axis and wherein the central axes of all of said passageways converge at a point outwardly of said outer face of said nozzle and in line with said enlarged central opening.

12. The digital odor generator as claimed in claim 11 further including means within said housing for passing fresh air through said central opening.

13. The digital odor generator as claimed in claim 11 wherein each of said odor compartments includes an odorant therein.

14. The digital odor generator as claimed in claim 13 further including a plurality of porous hollow cylinders adapted to fit within said odor compartments and wherein said odorants are located within each of said hollow cylinders.

15. The digital odor generator as claimed in claim 14 wherein said hollow cylinders are comprised of a porous plastic.

16. The digital odor generator as claimed in claim 13 including means for selectively forcing one or more odors through their respective odor compartments and out of said nozzle.

* * * * *